US012667363B2

(12) United States Patent
Solaun et al.

(10) Patent No.: US 12,667,363 B2
(45) Date of Patent: *Jun. 30, 2026

(54) HOOK WIRE FOR PREVENTING PREMATURE EMBOLIC IMPLANT DETACHMENT

(71) Applicant: DePuy Synthes Products, Inc., Raynham, MA (US)

(72) Inventors: Daniel Solaun, Miami, FL (US); David Blumenstyk, Miami, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 41 days.

This patent is subject to a terminal disclaimer.

(21) Appl. No.: 18/955,049

(22) Filed: Nov. 21, 2024

(65) Prior Publication Data

US 2025/0082335 A1 Mar. 13, 2025

Related U.S. Application Data

(63) Continuation of application No. 18/431,353, filed on Feb. 2, 2024, now Pat. No. 12,484,906, which is a
(Continued)

(51) Int. Cl.
 *A61B 17/12* (2006.01)
 *A61B 17/00* (2006.01)

(52) U.S. Cl.
 CPC .. *A61B 17/12113* (2013.01); *A61B 17/12145* (2013.01); *A61B 2017/12054* (2013.01)

(58) Field of Classification Search
 CPC ........ A61B 17/12113; A61B 17/12145; A61B 17/12031; A61B 17/1214;
(Continued)

(56) References Cited

U.S. PATENT DOCUMENTS 2,220,203 A 11/1940 Branin
3,429,408 A 2/1969 Maker et al.
(Continued)

FOREIGN PATENT DOCUMENTS

CN 102125451 A 7/2011
CN 103356260 A 10/2013
(Continued)

*Primary Examiner* — Tan-Uyen T Ho
*Assistant Examiner* — Lindsey R. Rivers
(74) *Attorney, Agent, or Firm* — Troutman Pepper Locke LLP

(57) ABSTRACT

Various systems and methods of delivering an implant to a target location of a body vessel are disclosed. A detachment system can include a tubular body including a lumen extending therethrough and a distal tube on a distal end of the tubular body. A loop wire can be affixed at a first end to the tubular body and can include a loop opening positioned approximate a distal end of the distal tube. A pull wire can extend through the lumen. A hook wire can extend radially through a sidewall of the distal tube and into the lumen. The hook wire can be positioned around a pull wire portion and tensioned such that the pull wire portion abuts the distal tube and provides frictional resistance between the pull wire portion and the sidewall of the distal tube. The frictional resistance can be effective to inhibit premature detachment of the implant.

20 Claims, 5 Drawing Sheets

Related U.S. Application Data continuation of application No. 17/685,147, filed on Mar. 2, 2022, now Pat. No. 11,937,825.

(58) Field of Classification Search

CPC ........ A61B 17/12022; A61B 17/12131; A61B 17/12177; A61B 2017/12054; A61B 2017/12172; A61F 2/011; A61F 2/9517; A61F 2002/9505; A61F 2002/9511

See application file for complete search history.

(56) References Cited

U.S. PATENT DOCUMENTS

| | | | |
|---|---|---|---|
| 4,368,730 A | 1/1983 | Sharrock | |
| 4,858,810 A | 8/1989 | Intlekofer et al. | |
| 5,069,674 A | 12/1991 | Fearnot et al. | |
| 5,108,407 A | 4/1992 | Geremia et al. | |
| 5,122,136 A | 6/1992 | Guglielmi et al. | |
| D329,698 S | 9/1992 | Loney et al. | |
| 5,234,437 A | 8/1993 | Sepetka | |
| 5,250,071 A | 10/1993 | Palermo | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,392,791 A | 2/1995 | Nyman | |
| 5,484,409 A | 1/1996 | Atkinson et al. | |
| 5,536,248 A | 7/1996 | Weaver et al. | |
| 5,569,221 A | 10/1996 | Houser et al. | |
| 5,645,558 A | 7/1997 | Horton | |
| 5,899,935 A | 5/1999 | Ding | |
| 5,925,059 A | 7/1999 | Palermo et al. | |
| 6,113,622 A | 9/2000 | Hieshima | |
| 6,203,547 B1 | 3/2001 | Nguyen et al. | |
| 6,391,037 B1 | 5/2002 | Greenhalgh | |
| 6,454,780 B1 | 9/2002 | Wallace | |
| 6,506,204 B2 | 1/2003 | Mazzocchi | |
| 6,561,988 B1 | 5/2003 | Turturro et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,384,407 B2 | 6/2008 | Rodriguez et al. | |
| 7,708,754 B2 | 5/2010 | Balgobin et al. | |
| 7,708,755 B2 | 5/2010 | Davis, III et al. | |
| 7,799,052 B2 | 9/2010 | Balgobin et al. | |
| 7,811,305 B2 | 10/2010 | Balgobin et al. | |
| 7,819,891 B2 | 10/2010 | Balgobin et al. | |
| 7,819,892 B2 | 10/2010 | Balgobin et al. | |
| 7,901,444 B2 | 3/2011 | Slazas | |
| 7,985,238 B2 | 7/2011 | Balgobin et al. | |
| 8,062,325 B2 | 11/2011 | Mitelberg et al. | |
| 8,333,796 B2 | 12/2012 | Tompkins et al. | |
| 8,926,650 B2 | 1/2015 | Que et al. | |
| 8,956,381 B2 | 2/2015 | Que et al. | |
| 9,155,540 B2 | 10/2015 | Lorenzo | |
| 9,232,992 B2 | 1/2016 | Heidner | |
| 9,314,326 B2 | 4/2016 | Wallace et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,120 B2 | 5/2017 | Lagodzki et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Paterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,918,718 B2 | 3/2018 | Lorenzo | |
| 10,149,676 B2 | 12/2018 | Mirigian et al. | |
| 10,285,710 B2 | 5/2019 | Lorenzo et al. | |
| 10,292,851 B2 | 5/2019 | Gorochow | |
| 10,420,563 B2 | 9/2019 | Hebert et al. | |
| 10,517,604 B2 | 12/2019 | Bowman et al. | |
| 10,668,258 B1 | 6/2020 | Calhoun et al. | |
| 10,806,402 B2 | 10/2020 | Cadieu et al. | |
| 10,806,461 B2 | 10/2020 | Lorenzo | |
| 11,951,026 B2 | 4/2024 | Clinger et al. | |
| 2001/0049519 A1 | 12/2001 | Holman et al. | |
| 2002/0072705 A1 | 6/2002 | Vrba et al. | |
| 2002/0165569 A1 | 11/2002 | Ramzipoor et al. | |
| 2002/0183786 A1 | 12/2002 | Girton | |
| 2003/0009208 A1 | 1/2003 | Snyder et al. | |
| 2003/0181942 A1 | 9/2003 | Sutton et al. | |
| 2004/0034363 A1 | 2/2004 | Wilson et al. | |
| 2004/0059367 A1 | 3/2004 | Davis et al. | |
| 2004/0087964 A1 | 5/2004 | Diaz et al. | |
| 2006/0025801 A1 | 2/2006 | Lulo et al. | |
| 2006/0064151 A1 | 3/2006 | Guterman | |
| 2006/0100687 A1 | 5/2006 | Fahey et al. | |
| 2006/0116711 A1 | 6/2006 | Elliott et al. | |
| 2006/0116714 A1 | 6/2006 | Sepetka et al. | |
| 2006/0135986 A1 | 6/2006 | Wallace et al. | |
| 2006/0206139 A1 | 9/2006 | Tekulve | |
| 2006/0241685 A1 | 10/2006 | Wilson et al. | |
| 2006/0247677 A1 | 11/2006 | Cheng et al. | |
| 2006/0276824 A1 | 12/2006 | Mitelberg et al. | |
| 2006/0276825 A1 | 12/2006 | Mitelberg et al. | |
| 2006/0276826 A1 | 12/2006 | Mitelberg et al. | |
| 2006/0276827 A1 | 12/2006 | Mitelberg et al. | |
| 2006/0276830 A1 | 12/2006 | Balgobin et al. | |
| 2006/0276833 A1 | 12/2006 | Balgobin et al. | |
| 2007/0010850 A1 | 1/2007 | Balgobin et al. | |
| 2007/0055302 A1 | 3/2007 | Henry et al. | |
| 2007/0083132 A1 | 4/2007 | Sharrow | |
| 2007/0203519 A1 | 8/2007 | Lorenzo et al. | |
| 2007/0233168 A1 | 10/2007 | Davis et al. | |
| 2007/0270903 A1 | 11/2007 | Davis, III et al. | |
| 2008/0027561 A1 | 1/2008 | Mitelberg et al. | |
| 2008/0045997 A1 | 2/2008 | Balgobin et al. | |
| 2008/0097462 A1 | 4/2008 | Mitelberg et al. | |

(56) References Cited

U.S. PATENT DOCUMENTS

| | | |
|---|---|---|
| 2008/0119887 A1 | 5/2008 | Que et al. |
| 2008/0269719 A1 | 10/2008 | Balgobin et al. |
| 2008/0269721 A1 | 10/2008 | Balgobin et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0099592 A1 | 4/2009 | Buiser et al. |
| 2009/0270877 A1 | 10/2009 | Johnson et al. |
| 2009/0312748 A1 | 12/2009 | Johnson et al. |
| 2010/0094395 A1 | 4/2010 | Kellett |
| 2010/0114017 A1 | 5/2010 | Lenker et al. |
| 2010/0206453 A1 | 8/2010 | Leeflang et al. |
| 2010/0324649 A1 | 12/2010 | Mattsson |
| 2011/0092997 A1 | 4/2011 | Kang |
| 2011/0118772 A1 | 5/2011 | Chen et al. |
| 2011/0118776 A1 | 5/2011 | Chen et al. |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2013/0338678 A1 | 12/2013 | Loushin et al. |
| 2014/0058435 A1 | 2/2014 | Jones et al. |
| 2014/0088565 A1 | 3/2014 | Vongphakdy et al. |
| 2014/0135812 A1 | 5/2014 | Divino et al. |
| 2014/0200607 A1 | 7/2014 | Sepetka et al. |
| 2014/0207175 A1 | 7/2014 | Aggerholm |
| 2014/0243883 A1 | 8/2014 | Tsukashima et al. |
| 2014/0277078 A1 | 9/2014 | Slazas et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0119884 A1 | 4/2015 | Fung et al. |
| 2015/0164666 A1 | 6/2015 | Johnson et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalacaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072165 A1 | 3/2017 | Lim et al. |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0071496 A1 | 3/2018 | Snyder et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |

(56) References Cited

U.S. PATENT DOCUMENTS

| | | |
|---|---|---|
| 2019/0192162 A1 | 6/2019 | Lorenzo et al. |
| 2019/0201688 A1 | 7/2019 | Olson |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0015876 A1 | 1/2020 | Chou et al. |
| 2020/0078024 A1 | 3/2020 | Tekulve |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2020/0406048 A1 | 12/2020 | Rentas Torres et al. |
| 2021/0001082 A1 | 1/2021 | Lorenzo et al. |
| 2021/0045759 A1 | 2/2021 | Merhi et al. |
| 2021/0085498 A1 | 3/2021 | Nygaard et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0220013 A1 | 7/2021 | Libarnes et al. |
| 2021/0338248 A1 | 11/2021 | Lorenzo et al. |
| 2021/0346002 A1 | 11/2021 | Lorenzo et al. |
| 2021/0353299 A1 | 11/2021 | Hamel et al. |

FOREIGN PATENT DOCUMENTS

| | | | |
|---|---|---|---|
| CN | 104203341 | A | 12/2014 |
| CN | 106456422 | A | 2/2017 |
| CN | 109770985 | A | 5/2019 |
| EP | 1985244 | A2 | 10/2008 |
| EP | 2498691 | | 9/2012 |
| EP | 3092956 | A1 | 11/2016 |
| EP | 3501427 | A1 | 6/2019 |
| EP | 3795097 | A1 | 3/2021 |
| EP | 3799803 | A1 | 4/2021 |
| EP | 3854321 | A1 | 7/2021 |
| EP | 1188414 | A1 | 3/2022 |
| EP | 4119065 | A1 | 1/2023 |
| JP | H10-507090 | A | 7/1998 |
| JP | 2006-334408 | A | 12/2006 |
| JP | 2006346350 | A | 12/2006 |
| JP | 2012-523943 | A | 10/2012 |
| JP | 2013-78584 | A | 5/2013 |
| JP | 2014-399 | A | 1/2014 |
| JP | 2016-179174 | A | 10/2016 |
| JP | 2017-529894 | A | 10/2017 |
| WO | WO 2007/070793 | A2 | 6/2007 |
| WO | WO 2008/064209 | A1 | 5/2008 |
| WO | WO 2009/132045 | A2 | 10/2009 |
| WO | WO 2012/158152 | A1 | 11/2012 |
| WO | WO 2016/014985 | A1 | 1/2016 |
| WO | WO 2017/066386 | A1 | 4/2017 |
| WO | WO 2018/022186 | A1 | 2/2018 |
| WO | WO 2020/148768 | A1 | 7/2020 |

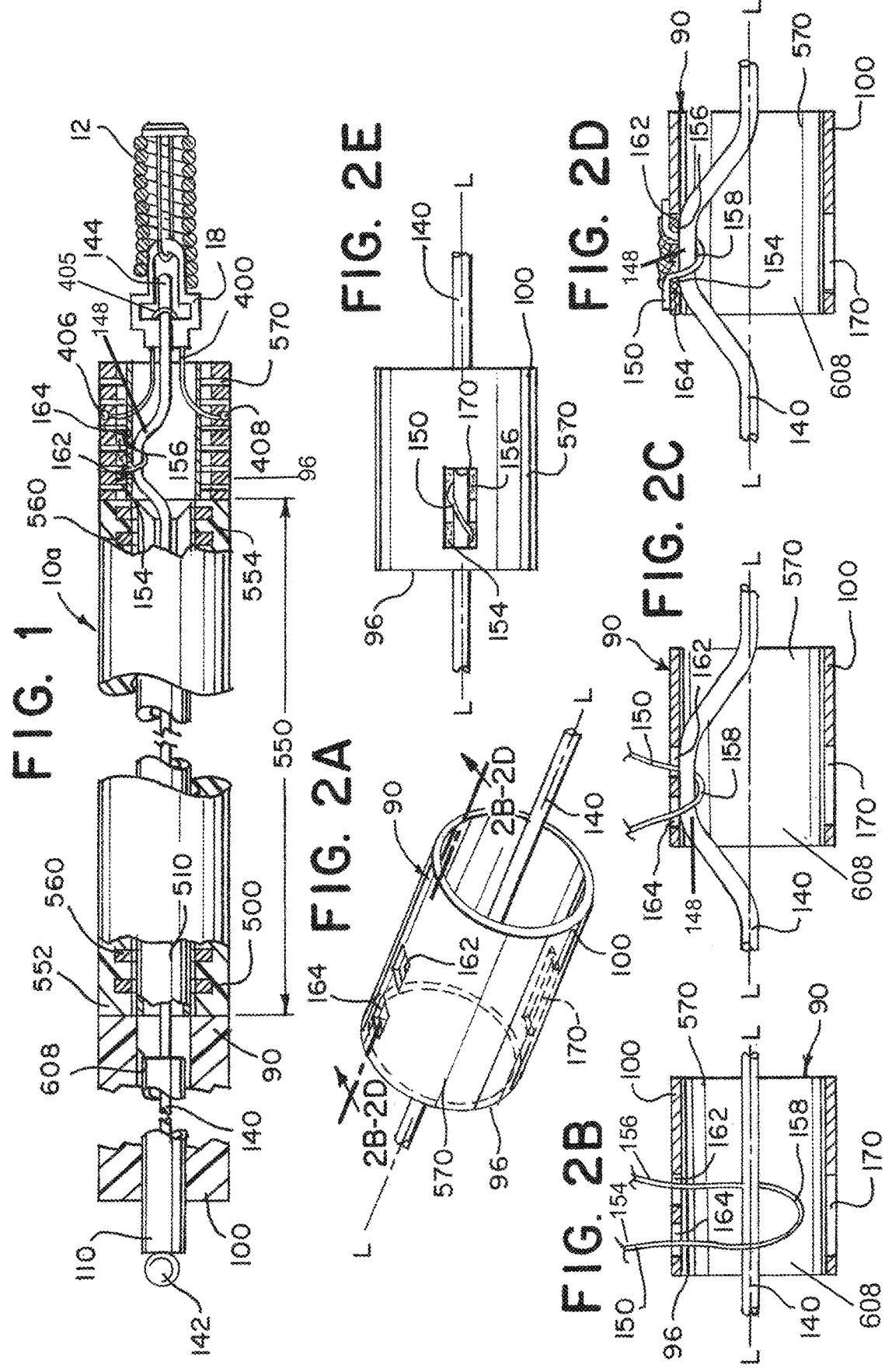

FIG. 6

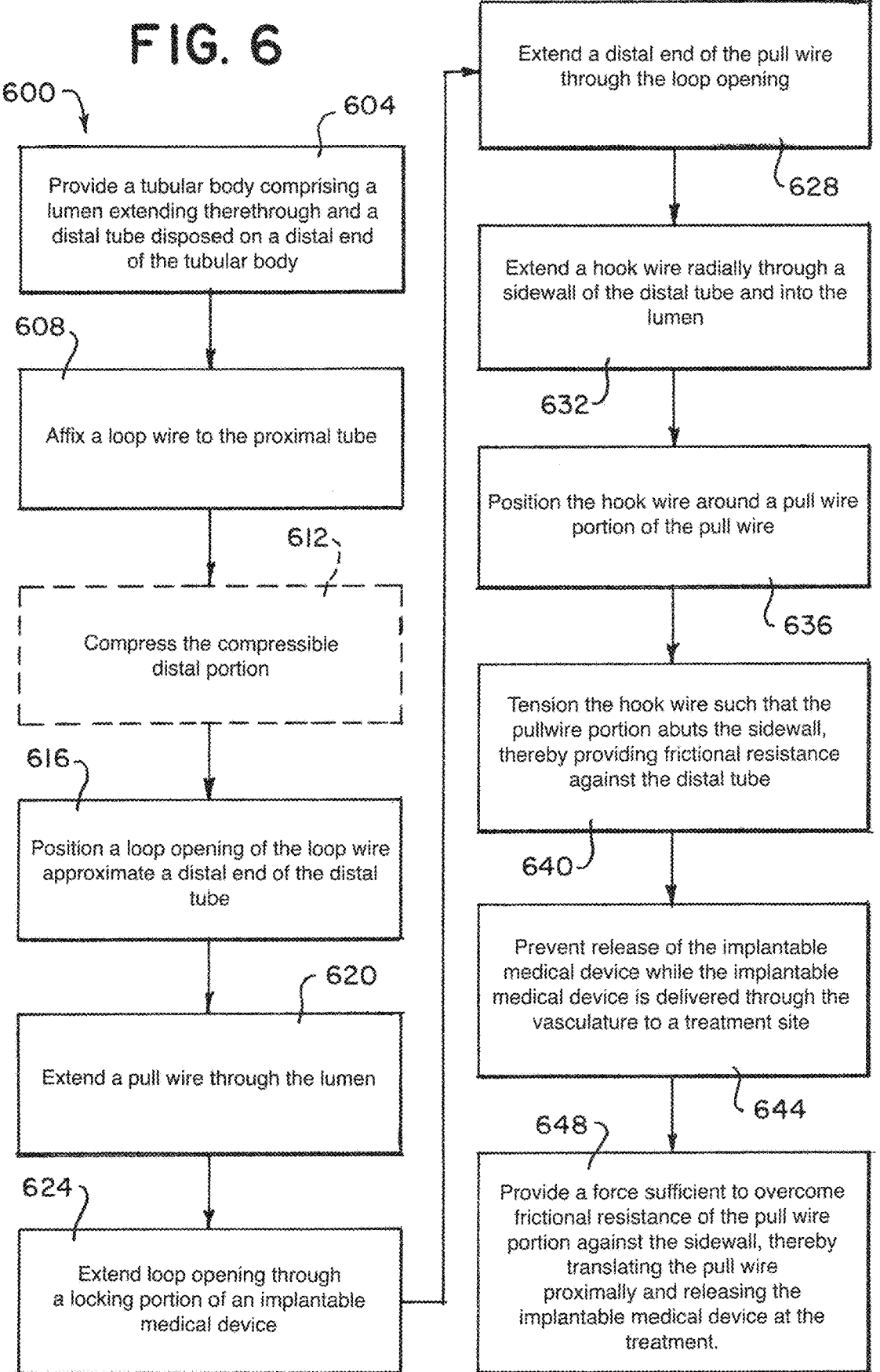

600

604

Provide a tubular body comprising a lumen extending therethrough and a distal tube disposed on a distal end of the tubular body

608

Affix a loop wire to the proximal tube

612

Compress the compressible distal portion

616

Position a loop opening of the loop wire approximate a distal end of the distal tube

620

Extend a pull wire through the lumen

624

Extend loop opening through a locking portion of an implantable medical device

Extend a distal end of the pull wire through the loop opening

628

Extend a hook wire radially through a sidewall of the distal tube and into the lumen

632

Position the hook wire around a pull wire portion of the pull wire

636

Tension the hook wire such that the pullwire portion abuts the sidewall, thereby providing frictional resistance against the distal tube

640

Prevent release of the implantable medical device while the implantable medical device is delivered through the vasculature to a treatment site

644

648

Provide a force sufficient to overcome frictional resistance of the pull wire portion against the sidewall, thereby translating the pull wire proximally and releasing the implantable medical device at the treatment.

HOOK WIRE FOR PREVENTING PREMATURE EMBOLIC IMPLANT DETACHMENT

CROSS REFERENCE TO RELATED APPLICATIONS

The present application is a continuation application of U.S. patent application Ser. No. 18/431,353 filed Feb. 2, 2024, which is a continuation application of U.S. patent application Ser. No. 17/685,147 filed Mar. 2, 2022, now U.S. Pat. No. 11,937,825 issued Mar. 26, 2024. The entire contents of which are hereby incorporated by reference.

FIELD OF INVENTION

The present invention relate to aneurysm treatment devices and more particularly, to improved delivery systems for embolic implants that prevent premature implant deployment.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

One issue with current catheter-based delivery systems is premature detachment of the implantable device. Premature detachment occurs when the implant is detached from the delivery system before reaching the treatment site. This may occur due to the tortuosity experienced by the delivery system as it passes through the vasculature of the patient, which can cause an increase in friction between the "pull wire" and the delivery system causing the pull wire to move proximally while the delivery system is moving distally.

Accordingly, there is a need for an improved implant delivery system that prevents premature detachment of the implant as it is delivered through tortuous vasculature. This disclosure is directed to this and other considerations.

SUMMARY

Various systems and methods of delivering an implant to a target location of a body vessel are disclosed. A detachment system can include a tubular body including a lumen extending therethrough and a distal tube on a distal end of the tubular body. A loop wire can be affixed at a first end to the tubular body and can include a loop opening positioned approximate a distal end of the distal tube. A pull wire can extend through the lumen. A hook wire can extend radially through a sidewall of the distal tube and into the lumen. The hook wire can be positioned around a pull wire portion and tensioned such that the pull wire portion abuts the distal tube and provides frictional resistance between the pull wire portion and the sidewall of the distal tube. The frictional resistance can be effective to inhibit premature detachment of the implant.

In one aspect, a detachment system for delivering an implantable medical device to a target location of a body vessel is disclosed. The detachment system can include a tubular body that includes a lumen extending therethrough and a distal tube that is disposed on a distal end of the tubular body. The detachment system can include a loop wire that includes a first end affixed to the tubular body and including a loop opening positioned approximate a distal end of the distal tube. The detachment system can include a pull wire extending through the lumen. The detachment system can include a hook wire that extends radially through a sidewall of the distal tube and into the lumen. The hook wire can be positioned around a pull wire portion of the pull wire and tensioned such that the pull wire portion abuts the distal tube to thereby provide frictional resistance between the pull wire portion and the sidewall of the distal tube. The loop wire and the pull wire can be positioned to secure the implantable medical device to the delivery system. The frictional resistance provided by the pull wire portion against the tubular body is effective to inhibit premature detachment of the implantable medical device as the implantable medical device is delivered by the detachment system to the target location of the body vessel.

In some embodiments, the hook wire includes hook wire ends that are welded to the distal tube. In some embodiments, the distal tube includes laser cut port holes in the sidewall. The hook wire can extend radially through each of the port holes and into the lumen of the distal tube. In some embodiments, the detachment system can include a laser cut window in the distal tube positioned opposite the laser cut port holes.

In some embodiments, the frictional resistance provided by the pull wire portion can be a force between approximately 5 gram-force and 25 gram-force.

In some embodiments, the loop wire and the pull wire are movable to release the implantable medical device from the detachment system.

In some embodiments, the hook wire can be stretch resistant.

In some embodiments, the pull wire can include a polytetrafluoroethylene (PTFE) coating.

In some embodiments, the distal tube includes a compressed distal portion and the loop opening is positioned approximate a distal end of the compressed distal portion.

In some embodiments, the loop wire is stretch resistant and the loop wire is under tension when the implantable medical device is secured to the detachment system.

In some embodiments, the tubular body includes a support coil that is disposed in a proximal direction from the distal tube.

In some embodiments, the hook wire includes a hook wire portion within the lumen of the distal tube and extending longitudinally along a longitudinal axis of the distal tube.

In another aspect, a method of using a detachment system is disclosed. The method can include providing a tubular body that includes a lumen extending therethrough and a distal tube disposed on a distal end of the tubular body. The method can include affixing a loop wire to the distal tube and positioning a loop opening in the loop wire approximate a distal end of the distal tube while the loop wire is affixed to the distal tube such that the loop wire is extended through the lumen. The method can include extending a pull wire through the lumen. The method can include extending the loop opening through a locking portion of an implantable medical device. The method can include extending a distal end of the pull wire through the loop opening. The method can include extending a hook wire radially through a sidewall of the distal tube and into the lumen. The method can include positioning the hook wire around a pull wire portion of the pull wire. The method can include tensioning the hook wire such that the pull wire portion abuts the sidewall to thereby provide frictional resistance against the distal tube. The method can include preventing, through frictional resistance of the pull wire portion against the distal tube, release of the implantable medical device while the implantable medical device is delivered through vasculature to a treatment site.

In some embodiments, the method can include providing a force sufficient to overcome the frictional resistance of the pull wire portion against the sidewall to thereby translate the pull wire proximally and release the implantable medical device at the treatment site.

In some embodiments, the method can include tensioning the pull wire portion against the sidewall with the hook wire to provide frictional resistance between approximately 5 gram-force and 25 gram-force.

In some embodiments, the method can include welding respective ends of the hook wire to the distal tube.

In some embodiments, extending a hook wire through the distal tube can include forming port holes through the sidewall and extending the hook wire radially through each of the port holes and into the lumen of the distal tube.

In some embodiments, the method can include forming a laser cut window in the distal tube positioned opposite the laser cut port holes.

In some embodiments, the distal tube can include a compressible distal portion such that the loop opening is approximate a distal end of the compressible distal portion, and the method further includes compressing the compressible distal portion.

In some embodiments, positioning the hook wire around a pull wire portion of the pull wire can include positioning a hook wire portion within the lumen of the tubular body that extends longitudinally along a longitudinal axis of the distal tube.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 an illustration of a detachment system and implant, according to aspects of the present invention.

FIGS. 2A-2E are illustrations of the process of inserting a hook wire into a lumen of a detachment system, positioning the hook wire around a pull wire portion, and tensioning the hook wire to cause the pull wire portion to abut a sidewall of the detachment system, according to aspects of the present invention.

FIG. 6 is a flowchart of an example method of using the detachment system, according to aspects of the present invention.

DETAILED DESCRIPTION

Figure 3:
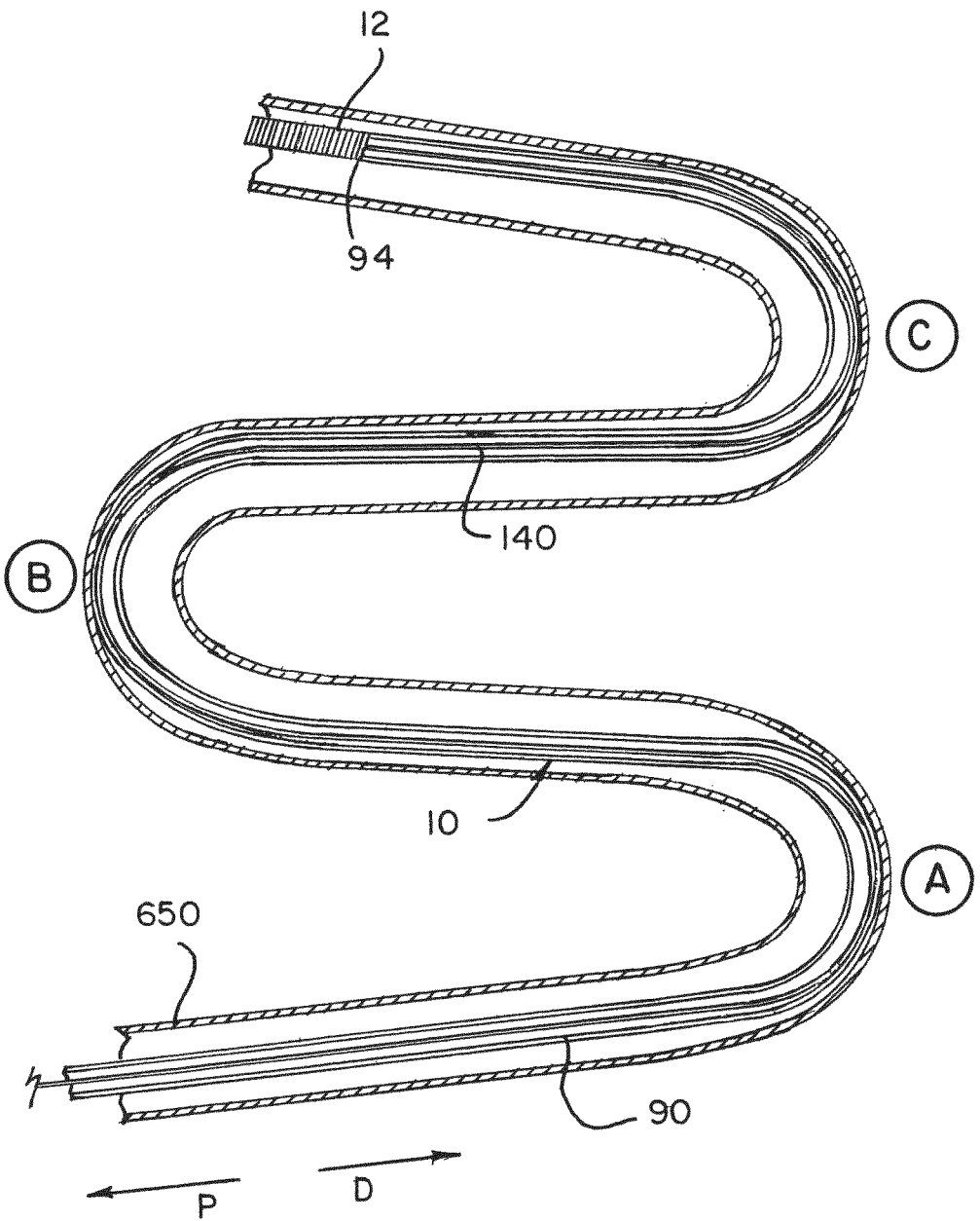
FIG. 3 is an illustration of a delivery system navigating a body lumen according to aspects of the present invention.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Turning to the figures, FIG. 1 shows an example detachment system 10 for deploying an implantable medical device 12 to a target location of a body vessel. The example detachment system 10 can include a proximal tube 100 having a tubular body 90, a support coil section 550 positioned distal to the proximal tube 100, and a distal tube 570 positioned distal to the support coil section 550. Support coil section 550 comprises a plurality of coils 560 and has a proximal end 552 and a distal end 554. The proximal tube 100, support coil section 550, and distal tube 570 may collectively have a lumen 608 extending therethrough. That is, lumen 608 extends from a proximal end of proximal tube 100, through support coil section 550, and through distal tube 570. Implant 12 can be positioned distal to the distal tube 570. Positioned within the lumen 608 of the support coil section 550 can be an inner support tube 510. Inner support tube 510 can be welded or otherwise attached to the inner sidewall of support coil section 550. Inner support tube 510 can provide structural support to the support coil section 550. The support coil section 550 can additionally be characterized by interference cuts from the sidewall of the support coil section 550. A sleeve 500 can surround the support coil section 550. A pull wire 140 can extend through the lumen 608 of delivery system 10. Within lumen 608 of proximal tube 100 can be positioned a proximal support tube 110. Proximal support tube 110 can be welded or otherwise attached to the inner sidewall of proximal tube 100. The pull wire 140 can include a pull wire bead 142 located on a proximal end of pull wire 140. The pull wire bead 142 can be sized such that the pull wire bead 142 is larger than the space between the proximal support tube 110 such that the pull wire bead 142 interferes with the proximal support tube 110 and proximal support tube 110 retains the pull wire bead 142 proximal to the proximal tube 100.

Located at a proximal end of distal tube 570 can be a plurality of port holes 162, 164 that are laser cut in the sidewall 96 of distal tube 570. A hook wire 150 can be positioned radially into the lumen orthogonal to a longitudinal axis defined by the delivery system 10 through the port holes 162, 164. The hook wire 150 can be positioned around a pull wire portion 148 of pull wire 140. Respective ends 154, 156 of the hook wire 150 can be attached to the sidewall 96 of distal tube 570 at the respective port holes 162, 164 using any method known in the pertinent art. For example, hook wire ends 154, 156 of hook wire 150 (as shown in FIGS. 2B-2E) can be welded to the sidewall 96 at port holes 162, 164. Hook wire 150 can be tensioned such that a pull wire portion 148 is pulled into contact and abuts sidewall 96 of distal tube 570. The pull wire portion 148 can provide a frictional resistance to proximal translation of the pull wire 140 as the detachment system 10 navigates tortuous vasculature to a treatment site. According to some embodiments, a laser cut window 170 (as shown in FIGS. 2B-2E) may be formed in the sidewall 96 of distal tube 570 opposite to the port holes 162, 164.

A loop wire opening 405 of loop wire 400 can be located at a distal portion 404 of loop wire 400 and can extend through a locking member 18 of implant 12. The distal end 144 of pull wire 140 can be positioned through the loop wire opening 405 of loop wire 400 to secure implant 12 to the delivery system 10. The proximal ends 406, 408 of loop wire 400 can be attached to the sidewall 96 of the distal tube 570. The attachment can be of any kind known in the pertinent art, including but not limited to welding proximal ends 406, 408 to the distal tube 570 sidewall 96 and/or gluing proximal ends 406, 408 to the distal tube. The loop wire 400 can be effective to hold the compressible distal section 300 (as shown in FIGS. 5A-5D) of distal tube 570 in compression until implant 12 is released from the detachment system 10.

When the delivery system 10 is assembled, the support coil section 550 and sleeve 500 can be more flexible than the distal tube 570 and the proximal tube 100. One way to measure flexibility is to perform a three-point bend test wherein a portion of the delivery system 10 is held fixed at two end points, a force is applied perpendicularly to the delivery system 10 centrally between the points, and flexibility is quantified by the length of deflection of the delivery system 10 caused by the force. When measured in this way, in some examples, the support coil section 550 and sleeve 500 can be about 1.5 times more flexible than the distal tube 570 and about 20 times more flexible than the proximal tube 100. That is, when the three-point test is performed identically on the three sections 100, 550, and 570, the support coil section 550 deflects over a length that is about 1.5 times the deflection of the distal tube 570 and about 20 times the length of deflection of the proximal tube 100. Flexibility can be measured in other ways as would be appreciated and understood by a person having pertinent skill in the requisite art. When the detachment system 10 is assembled, the support coil section 550 and sleeve 500 can be more flexible than the distal tube 570 and the proximal tube 100 as flexibility is determined by other means as would be known to a person of ordinary skill in the art.

According to some embodiments, the distal tube 570 can include a compressible distal portion 300 as shown in FIGS. 5A-5D, which can be compressed and formed from a spiral-cut portion of the distal tube 570, formed by a laser cutting operation. Additionally, or alternatively, the compressible distal portion 300 can be formed of a wound wire, spiral ribbon, or other arrangement allowing axial adjustment according to the present invention. Preferably, compressible distal portion 300 is in the elongated condition at rest and automatically or resiliently returns to the elongated condition from a compressed condition, unless otherwise constrained. In some embodiments, the loop wire 400 is effective to hold the compressed distal portion 300 in compression while the implant 12 is delivered to the treatment site.

Pull wire 140 can be constructed out of any suitable material, for example, pull wire 140 can be constructed of stainless steel or memory shape material, such as nitinol. According to some embodiments, pull wire 140 can additionally be coated with polytetrafluoroethylene (PTFE). According to some embodiments, a PTFE coating can be selectively removed from the pull wire portion 148 to increase frictional resistance that the pull wire portion 148 provides against sidewall 96.

FIGS. 2A-2E are illustrations of the process of inserting a hook wire into a lumen of a detachment system, positioning the hook wire around a pull wire portion, and tensioning the hook wire to cause the pull wire portion to abut a sidewall of the detachment system, according to aspects of the present invention. As shown in FIG. 2A, hook wire 150 can be positioned orthogonal to the longitudinal axis L-L defined by the tubular body 90 of detachment system 10. The hook wire 150 can be positioned radially into lumen 608 through laser cut window 170. As shown in FIG. 1A, hook wire 150 can be positioned around a pull wire portion 148 of pull wire 140. Respective ends 154, 156 of hook wire 150 can extend through port holes 162, 164, as shown in FIG. 2B. FIG. 2C shows the hook wire 150 pulled tightly against the pull wire portion 148 of pull wire 140 such that pull wire portion 148 abuts the sidewall 96 of distal tube 570. A hook wire portion 158 of hook wire 150 can be seen positioned within the lumen 608 of tubular body 90 such that the hook wire portion 158 extends along longitudinal axis L-L while a remainder of the hook wire portion 150 is approximately orthogonal to the longitudinal axis L-L. In FIG. 2D, respective ends 154, 156 of hook wire 150 are welded, glued, or otherwise attached to the sidewall 96 of distal tube 570 using any method known in the pertinent art. Hook wire ends 154, 156 can be seen attached by welds in FIG. 2D approximate the port holes 162, 164 within sidewall 96. FIG. 2E shows the position of pull wire portion 148 against sidewall 96 as can be seen through laser cut window 170 that is positioned opposite port holes 162, 164.

FIG. 3 illustrates positioning of an implant 12 such as an embolic coil suitable for aneurysm treatment, a guide catheter 650, and a delivery system 10 including a tubular body 90 and a pull wire 140 within tortuous vasculature (vasculature not illustrated). At bends A, B, and C, the tubular body 90 can extend to a sidewall of the guide catheter 650 on each outer curve of each bend, and likewise, the pull wire 140 can extend to a sidewall of the tubular body 90 on each outer curve of each bend. During a procedure, the tubular body 90 and pull wire 140 can be fed into the guide catheter 650 in the distal direction D, first passing through bend A, then bend B, and then bend C. As the tubular body 90 and pull wire 140 navigate the bends, the pull wire 140 is prevented from translating proximally with respect to the tubular body. The frictional resistance caused by the pull wire portion 148 held against sidewall 96 of distal tube 570 as shown in FIG. 1 provides a resistance to the proximal drift that the pull wire 140 can otherwise experience while the detachment system is delivered through the tortuous vasculature to a treatment site. As pull wire 140 is "pulled" proximally during navigation of the vasculature, this force is resisted and balanced by the frictional resistance caused by the tensioned hook wire 150 holding pull wire portion 148 tightly against the sidewall 96 of distal tube 570. The amount of frictional resistance provided by the pull wire portion 148 can be varied as would be understood by a person having pertinent skill in the art, by varying the size of pull wire 140, varying the materials of pull wire 140, varying the size of pull wire portion 148, varying the tension of hook wire 150 against pull wire portion 148, and/or adding or selectively removing a coating of pull wire 140, such as polytetrafluoroethylene (PTFE).

Figure 4:
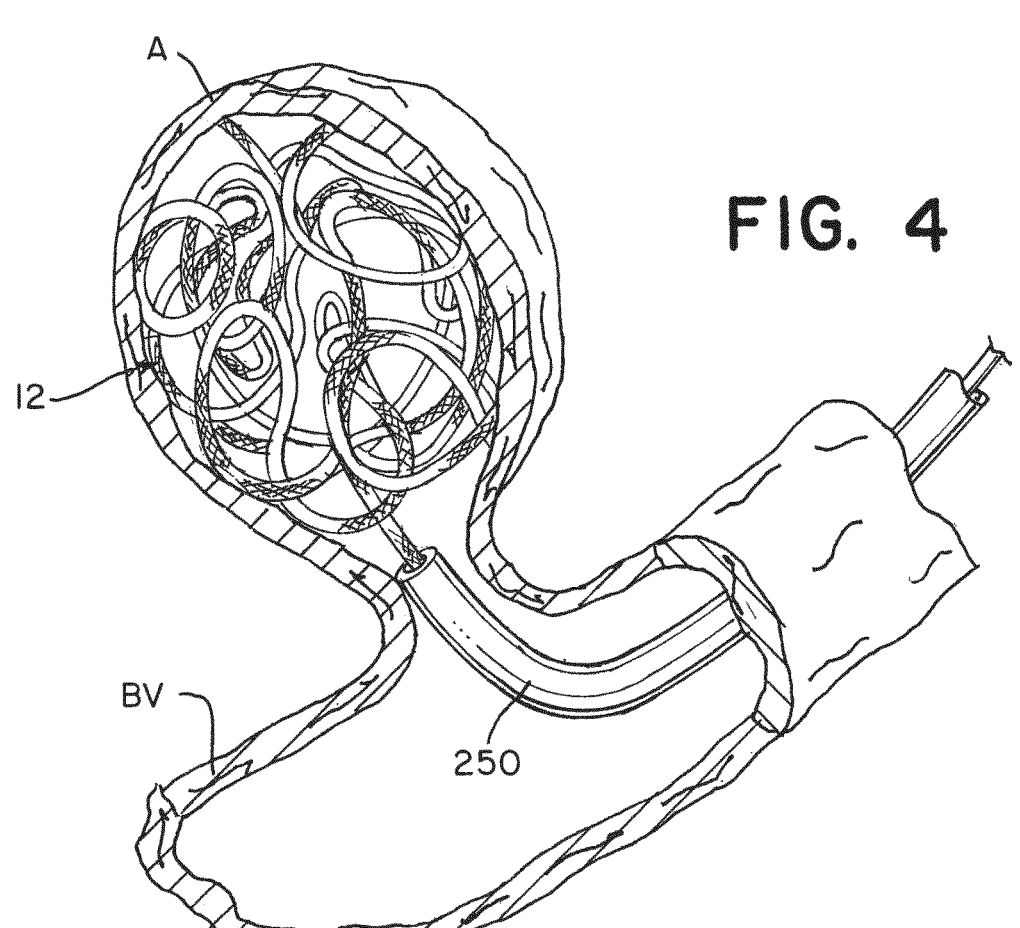
FIG. 4 is an illustration of embolic coils being positioned within an aneurysm according to aspects of the present invention.

FIG. 4 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

Figure 5A:
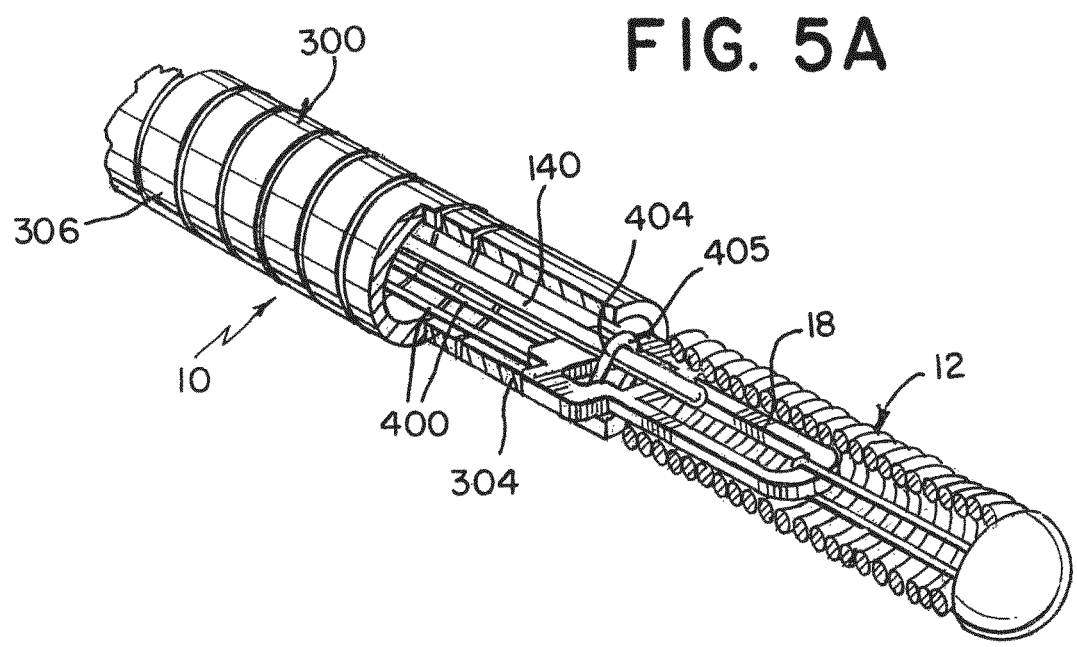
FIGS. 5A-5D illustrate a sequence of steps for releasing an embolic implant from the delivery member, according to aspects of the present invention.
Figures 5B, 5C, 5D:
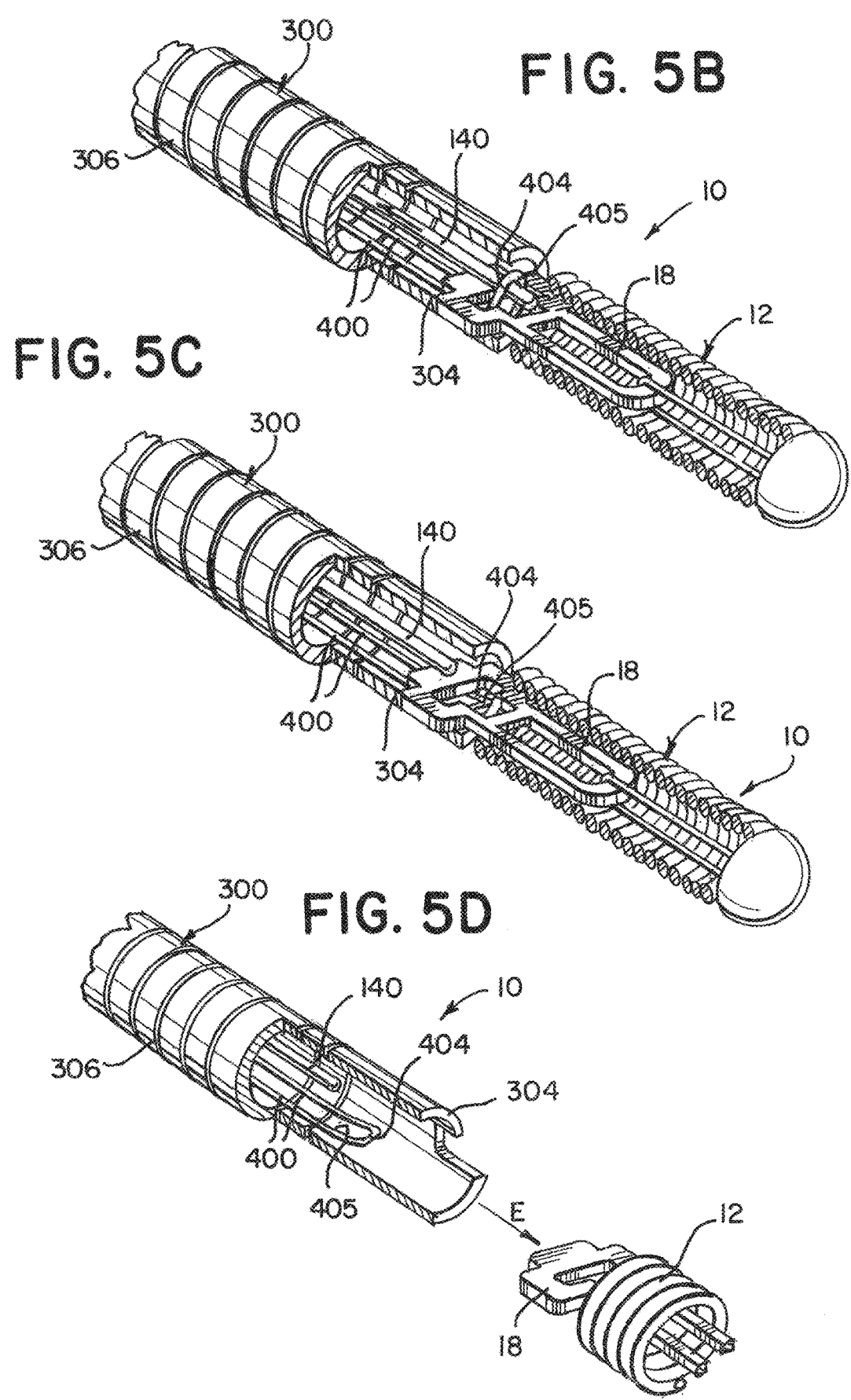

FIGS. 5A-5D illustrate a time sequence of steps for releasing an embolic implant 12 from a delivery system 10. The detachment system 10 can be configured such as illustrated in the previous figures and as otherwise described herein. FIG. 5A illustrates an engagement system including the loop wire 400 and pull wire 140 locked into a locking portion 18 of the medical device 12. The spiral cuts 306 of the compressible distal portion 300 can be compressed and the loop wire opening 405 at a distal end 404 of the loop wire 400 can be placed through the locking portion 18. When the pull wire 140 is put through the loop wire opening 405 the medical device 12 is now secure. FIG. 5B illustrates the pull wire 140 being drawn proximally to begin the release sequence for the medical device 12. FIG. 5C illustrates the instant the distal end 144 of the pull wire exits the loop wire opening 405 and the pull wire 140 is pulled free of the loop wire 400. The distal end 404 of the loop wire 400 falls away and exits the locking portion 18. As can be seen, there is now nothing holding the medical device 12 to the detachment system 10. FIG. 5D illustrates the end of the release sequence. Here, the compressible portion 300 has extended/ returned to its original shape and "sprung" forward. An elastic force E is imparted by the distal end 305 of the compressible distal portion 300 to the medical device 12 to "push" it away to ensure a clean separation and delivery of the medical device 12.

The compressible portion 300 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the compressible distal portion 300.

FIG. 6 is a flowchart of an example method of using the detachment system, according to aspects of the present invention. In block 604, the method can include providing a tubular body 90. The tubular body can include a lumen 608 extending therethrough and a distal tube 570 disposed on a distal end 94 of the tubular body 90. In some embodiments, the distal tube 570 can include a compressible distal section 300 characterized by spiral cuts 306 made within the distal tube 570. In block 608, the method can include affixing a loop wire 400 to the distal tube 570. Loop wire ends 406, 408 of loop wire 400 can be affixed to the distal tube 570 as shown in FIG. 1.

In optional block 612, the distal tube 570 can include a compressible distal portion 300 such that the loop wire opening 405 is approximate a distal end 304 of the compressible distal portion. The method can include compressing the compressible distal portion 300 of the distal tube 570.

In block 616, the method can include positioning a loop wire opening 405 of the loop wire 400 approximate a distal end of the distal tube 570 while the loop wire is affixed to the distal tube 570 such that the loop wire is extended through the lumen 608. In block 620, a pull wire 140 can be extended through the lumen 608. In block 624, the method can include extending a loop wire opening 405 through a locking portion 18 of an implantable medical device 12. In block 628, the method can include extending a distal end 144 of the pull wire 140 through the loop opening. In this configuration, the implantable medical device 12 is secured to the detachment system 10. In block 632, the method can include extending a hook wire 150 radially through a sidewall 96 of the distal tube 570 and into the lumen 608. In block 636, the hook wire 150 can be positioned around a pull wire portion 148 of the pull wire 140. In block 640, the hook wire 150 can be tensioned such that the pull wire portion 148 abuts the sidewall 96 of distal tube 570. The pull wire portion 148 can provide a frictional resistance against the distal tube as the hook wire 150 holds the pull wire portion 148 under tension against the sidewall 96.

In block 644, the method can include preventing the release of the implantable medical device 12 while the implantable medical device 12 is delivered through vasculature to a treatment site. For example, as shown in FIG. 3, the detachment system 10 and implant implantable medical device 12 can travel through tortuous vasculature through bends A, B, C. As the detachment system moves around example bends A, B, C, pull wire 140 can be prevented from translated proximally with respect to the tubular body 90 due to the frictional resistance of pull wire portion 148 against sidewall 96 of distal tube 570. In block 648, the method can include providing a force sufficient to overcome the frictional resistance of the pull wire portion 148 against the sidewall 96. The force can cause the pull wire 140 to be translated proximally, which allows distal end 144 to exit loop wire opening 405 of loop wire 140, thereby allowing the implantable medical device 12 to be released from the detachment system 10, for example, as shown in FIG. 5D.

In some embodiments, the method can include tensioning the pull wire portion 148 against the sidewall 96 with the hook wire 150 to provide frictional resistance between approximately 5 gram-force and 25 gram-force.

In some embodiments, the method can include welding respective ends 154, 156 of the hook wire 150 to the distal tube 570. In some embodiments, positioning the hook wire 150 around a pull wire portion 148 of the pull wire 140 can further include positioning a hook wire portion 158 within the lumen 608 of the distal tube 570 that extends longitudinally along a longitudinal axis L-L of the distal tube 570.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A detachment system for delivering an implantable medical device to a target location of a body vessel, the detachment system comprising:

a tubular body and a distal tube disposed on the end of the tubular body, wherein a lumen extends through the tubular body and the distal tube;

a loop wire comprising a first end affixed to the tubular body and comprising a loop opening positioned approximate a distal end of the distal tube;

a pull wire extending through the lumen;

a hook wire extending radially through a sidewall of the distal tube and into the lumen, the hook wire positioned around a pull wire portion of the pull wire and tensioned such that the pull wire portion abuts the distal tube; and a sleeve surrounding at least a proximal portion of the tubular body;

wherein the loop wire and the pull wire are positioned to secure the implantable medical device to the detachment system.

2. The detachment system of claim 1, wherein the hook wire comprises hook wire ends that are welded to the distal tube.

3. The detachment system of claim 1, wherein the distal tube comprises port holes in the sidewall, the hook wire extending radially through each of the port holes and into the lumen.

4. The detachment system of claim 3, further comprising a window in the distal tube positioned opposite the port holes.

5. The detachment system of claim 1, wherein a frictional resistance provided by the pull wire portion comprises a force between approximately 5 gram-force and 25 gram-force.

6. The detachment system of claim 1, wherein the loop wire and the pull wire are movable to release the implantable medical device from the detachment system.

7. The detachment system of claim 1, wherein the hook wire is stretch resistant.

8. The detachment system of claim 1, wherein the pull wire comprises a polytetrafluoroethylene coating.

9. The detachment system of claim 1, wherein the distal tube comprises a compressed distal portion and the loop opening is positioned approximate a distal end of the compressed distal portion.

10. The detachment system of claim 1, wherein the loop wire is stretch resistant, and wherein the loop wire is under tension when the implantable medical device is secured to the detachment system.

11. The detachment system of claim 1, wherein the tubular body further comprises a support coil disposed in a proximal direction from the distal tube.

12. The detachment system of claim 11, wherein the hook wire comprises a hook wire portion positioned within the lumen and extending longitudinally along a longitudinal axis of the distal tube.

13. A method comprising:

providing a tubular body and a distal tube disposed on the end of the tubular body, wherein a lumen extends through the tubular body and the distal tube;

positioning a sleeve around at least a proximal portion of the tubular body;

affixing a loop wire to the distal tube;

positioning a loop opening in the loop wire approximate a distal end of the distal tube while the loop wire is affixed to the distal tube such that the loop wire is extended through the lumen;

extending a pull wire through the lumen;

extending the loop opening through a locking portion of an implantable medical device;

extending a distal end of the pull wire through the loop opening;

extending a hook wire radially through a sidewall of the distal tube and into the lumen;

positioning the hook wire around a pull wire portion of the pull wire;

tensioning the hook wire such that the pull wire portion abuts the sidewall; and preventing release of the implantable medical device while the implantable medical device is delivered through vasculature to a treatment site.

14. The method of claim 13, further comprising:

providing a force sufficient to overcome a frictional resistance of the pull wire portion against the sidewall, thereby translating the pull wire proximally and releasing the implantable medical device at the treatment site.

15. The method of claim 13, further comprising:

tensioning the pull wire portion against the sidewall with the hook wire to provide a frictional resistance between approximately 5 gram-force and 25 gram-force.

16. The method of claim 13, further comprising welding respective ends of the hook wire to the distal tube.

17. The method of claim 13, wherein extending the hook wire radially through the distal tube further comprises forming port holes through the sidewall, the hook wire extending radially through each of the port holes and into the lumen.

18. The method of claim 17, further comprising forming a window in the distal tube positioned opposite the port holes.

19. The method of claim 13, wherein the distal tube comprises a compressible distal portion such that the loop opening is approximate a distal end of the compressible distal portion, and the method further comprises compressing the compressible distal portion.

20. The method of claim 13, wherein positioning the hook wire around the pull wire portion of the pull wire further comprises positioning a hook wire portion within the lumen that extends longitudinally along a longitudinal axis of the distal tube.

* * * * *